United States Patent [19]

Renken et al.

[11] Patent Number: 4,618,717

[45] Date of Patent: Oct. 21, 1986

[54] CATALYTIC PROCESS FOR THE PRODUCTION OF PRIMARY AMINES FROM OXYETHYLENE GLYCOL MONOALKYL ETHERS

[75] Inventors: Terry L. Renken; John F. Knifton, both of Austin, Tex.

[73] Assignee: Texaco Inc., White Plains, N.Y.

[21] Appl. No.: 651,372

[22] Filed: Sep. 17, 1984

[51] Int. Cl.$^4$ .............................................. C07C 89/02
[52] U.S. Cl. .................................................... 564/475
[58] Field of Search ......................................... 564/475

[56] References Cited

U.S. PATENT DOCUMENTS

| | | | |
|---|---|---|---|
| 2,928,877 | 3/1960 | Marion et al. | 260/585 |
| 3,128,311 | 4/1964 | Shirley et al. | 260/585 |
| 3,390,184 | 6/1968 | Moss et al. | 260/585 |
| 3,654,370 | 4/1972 | Yeakey | 260/584 |
| 4,014,933 | 3/1977 | Boettger et al. | 260/563 |
| 4,153,581 | 5/1979 | Habermann | 252/472 |

FOREIGN PATENT DOCUMENTS 0017651 10/1980 European Pat. Off. .

Primary Examiner—Charles F. Warren
Assistant Examiner—Elizabeth A. Flaherty
Attorney, Agent, or Firm—Jack H. Park; Kenneth R. Priem

[57] ABSTRACT

A process for the conversion of oxyethylene glycol monoalkyl ethers to the corresponding primary amines by reaction with ammonia in the presence of a nickel-copper-chromium-containing catalyst.

8 Claims, No Drawings

CATALYTIC PROCESS FOR THE PRODUCTION OF PRIMARY AMINES FROM OXYETHYLENE GLYCOL MONOALKYL ETHERS

BACKGROUND OF THE INVENTION

1. Field of the Invention

This invention relates to an improved process for the production of primary amines from oxyalkylene glycol monoalkyl ethers. More particularly, this invention relates to a catalytic process for the substantially selective conversion of oxyethylene glycol monoalkyl ethers to primary amines wherein the monoalkyl ether is brought into contact with a catalyst containing nickel, copper and at least one of the oxides of chromium, iron, titanium, thorium, zinc, zirconium or manganese in the presence of about 4 to about 25 moles of ammonia per mole of monoalkyl ether and about 0.01 to about 1 mole of hydrogen per mole of monoalkyl ether at a temperature within the range of about 175° to about 250° C. and a pressure within the range of about 500 to about 5000 psig.

2. Prior Art

Marion et al. U.S. Pat. No. 2,928,877 describe the low pressure vapor phase amination of oxyalkylene glycol monoalkyl ethers over a hydrogenation/dehydrogenation catalyst in a hydrogen atmosphere. The disadvantage of this process is the rather high yield of secondary amine along with the desired primary amine.

Shirley et al. U.S. Pat. No. 3,128,311 is directed to a higher pressure process for the conversion of aliphatic alcohols to amines using a catalyst of the class described above in the presence of ammonia and hydrogen. The starting material for the Shirley et al. process is an aliphatic alcohol containing 1 to 20 carbon atoms. The reaction is conducted over a temperature range of about 180° to about 275° C. and in the presence of a comparatively large amount of added hydrogen. The partial pressure of hydrogen was in the range of 30% to 85% of the total pressure in the system. Shirley et al. used about 1 to about 8 moles of ammonia per mole of alcohol. The patentees reported comparatively high yields of primary amines of about 55 to about 80% at conversions of the alcohol ranging from about 50 to about 95%.

SUMMARY OF THE INVENTION

It has been discovered in accordance with the present invention that the Shirley et al. process is not entirely satisfactory when it is desired to convert oxyethylene monoglycol ethers to primary amines. The oxyethylene glycol monoethers contain ether groups which are susceptible to rupture during a conversion operation. Moreover, it is desirable that the yield of primary amines in such a process be within the range of about 85 to 95% at a comparatively high conversion level of about 40 to about 80%, based on the oxyethylene glycol monoalkyl ether starting material.

This is accomplished in accordance with the present invention, however, by using a catalyst of the type contemplated by Shirley et al., namely, a catalyst containing as the active components, from about 50 to about 90 wt. % of nickel, from about 10 to about 50 wt. % of copper and from about 0.5 to about 5 wt. % of an oxide selected from the class consisting of chromium oxide, iron oxide, titanium oxide, thorium oxide, magnesium oxide, zinc oxide, zirconium and manganese oxide. A preferred group of such catalysts contain from about 70 to about 77 wt. % of nickel, about 20 to about 25 wt. % of copper and about 2 to about 5 wt. % of chromium oxide (calculated as the metal).

The feed materials for the present invention are ammonia, hydrogen and an oxyethylene glycol monoether having formula (I),

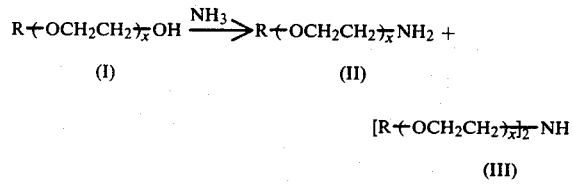

(I)      (II)

$$[R{+}OCH_2CH_2{\overline{)_x}}]_{\overline{2}}NH$$

(III)

wherein R is an alkyl group containing 1 to 10 carbon atoms and x is an integer having a value of about 1 to about 5.

Examples of such alkylether starting materials include, for example, ethylene glycol monomethyl ether, ethylene glycol monoethyl ether, ethylene glycol n-propyl ether, ethylene glycol isopropyl ether, ethylene glycol n-butyl ether, ethylene glycol isobutyl ether, ethylene glycol t-butyl ether, etc. and the corresponding diethylene, triethylene, tetraethylene and pentaethylene glycol ethers.

The process of the present invention is suitably conducted in the presence of about 4 to about 25 moles of ammonia per mole of oxyalkylene glycol monoethyl ether. Preferably, from about 6 to about 14 moles of ammonia per mole of oxyalkylene glycol monoethyl ether are used.

Hydrogen, in small amounts, is also a necessary feed component for the present invention. Suitably, from about 0.01 to about 1 mole of hydrogen per mole of oxyalkylene glycol monoalkyl ether feedstock is employed. More preferably, from about 0.3 to about 0.7 mole of hydrogen per mole of oxyalkylene glycol monoalkyl ether is employed. In contrast to the prior work of Shirley et al., it has been found that in the case of glycol monalkyl ether amination, superior yields of desired primary amine product (II) are realized when the hydrogen partial pressure in the reactor is less than 30%. In the examples where the hydrogen partial pressure is raised to 30%, the yield of primary amine is substantially lower.

The reaction is suitably conducted under comparatively moderate pressure conditions of about 500 to about 5000 psig.

The process of the present invention may be conducted batchwise using an autoclave containing powdered catalyst, or it may be conducted continuously by passing the feed materials over a bed of pelleted catalyst. When the process of the present invention is conducted continuously, the desired molar ratios of ammonia and hydrogen to oxyalkylene glycol monoalkyl ether can be established and maintained by regulating the rates at which the feed components are fed to the reactor.

The reaction mixture formed as a result of the reductive amination of the oxyethylene glycol monoalkyl ether may be recovered and fractionated in any suitable manner, such as by fractional distillation, to obtain the desired primary amine product.

DETAILED DESCRIPTION OF THE PREFERRED EMBODIMENT OF THE PRESENT INVENTION

The present invention is further illustrated by the following specific examples which are given by way of illustration and which are not intended as limitations on the scope of this invention.

EXAMPLE 1

A Ni-Cu-Cr catalyst containing approximately 77 wt. % Ni, 12 wt. % Cu and 2 wt. % Cr ($\frac{1}{8}$" diameter × - " pellets, 100 cc) was charged to a 0.516" ID tubular upward flow reactor. A pre-mixed feed composed of 10/1 (mol/mol) ammonia/2-butoxyethanol was pumped through the catalyst bed at a rate of ca. 0.62 lb/hr (0.98 mol/hr. of alcohol, 9.80 mol/hr of ammonia). Hydrogen was also passed through the reactor at a steady rate of 0.045 mol/hr. The pressure was maintained at 2500 psig. Liquid samples corresponding to several reactor temperatures were analyzed by gas chromatography on a water and ammonia free basis. The results of these analyses along with appropriate reactor conditions are in Table I.

TABLE I

| Temp, °C. | 190 | 200 | 210 | 220 | 230 | 240 |
|---|---|---|---|---|---|---|
| LHSV, g/hr/cc cat | 2.6 | 2.7 | 2.7 | 2.8 | 2.8 | 2.6 |
| % 2-butoxyethanol conversion | 24.3 | 38.2 | 57.0 | 72.9 | 85.7 | 93.4 |
| % Selectivities: | | | | | | |
| 2-butoxethylamine | 98.7 | 98.2 | 96.7 | 93.8 | 86.7 | 74.7 |
| bis(2-butoxyethyl)amine | 0.3 | 0.7 | 1.8 | 3.9 | 7.4 | 10.5 |

EXAMPLE 2

Another run was performed using the reactor and reaction conditions described above and a reactor temperature of 225° C. Reactor effluent corresponding to a throughput of ca. 2690.5 g of 2-butoxyethanol feed was collected. Distillation of this material afforded 515.7 g of 2-butoxyethanol (bp 165°-169° C.), which corresponded to 80.8% conversion. Also obtained was 1613.6 g of 2-butoxyethylamine (bp 151°-155° C.), which corresponded to a 74.8% yield based on alcohol consumed. Some dark residue (209.1 g) remained in the distillation pot. Gas chromatographic analysis indicated this material contained ca. 42.3% bis(2-butoxyethyl)amine.

EXAMPLE 3

A pre-mixed feed composed of 10/1 (mol/mol) ammonia/2-(2-methoxyethoxy)ethanol was pumped through the same catalyst bed and reactor system of Example 1 at a rate of ca. 0.62 lb/hr. Hydrogen was also passed through the reactor at various feed rates. The pressure was maintained at 2500 psig. Liquid samples corresponding to several reactor temperatures at each of three different hydrogen feed rates were analyzed by gas chromatography on a water and ammonia free basis. The results of these analyses along with appropriate reactor conditions are given in Table II.

TABLE II

| Mol H$_2$/ Mol Alcohol | Mol NH$_3$/ Mol H$_2$ | | Reactor Temperature, °C. | | | |
|---|---|---|---|---|---|---|
| | | | 190 | 200 | 210 | 220 |
| 0.048 | 210 | % Alcohol Conversion | 26.6 | 40.8 | 63.4 | 80.0 |
| | | % Primary Amine | 98.7 | 97.5 | 93.5 | 81.5 |
| | | % Secondary Amine | 0.4 | 1.0 | 2.8 | 7.0 |
| 0.48 | 21 | % Alcohol Conversion | 30.3 | 54.9 | 76.4 | 89.5 |
| | | % Primary Amine | 96.0 | 92.1 | 86.1 | 80.1 |
| | | % Secondary Amine | 3.4 | 7.2 | 13.0 | 17.5 |
| 1.3 | 7.8 | % Alcohol Conversion | 31.2 | 55.7 | 77.3 | 90.8 |
| | | % Primary Amine | 91.6 | 85.1 | 79.3 | 72.9 |
| | | % Secondary Amine | 7.8 | 13.6 | 18.8 | 23.9 |

TABLE III

| Mol H$_2$/ Mol Alcohol | Mol NH$_3$/ Mol H$_2$ | | Reactor Temperature, °C. | | | |
|---|---|---|---|---|---|---|
| | | | 190 | 200 | 210 | 220 |
| 0.068 | 145 | % Alcohol Conversion | 31.3 | 48.9 | 64.1 | 79.1 |
| | | % Primary Amine | 93.4 | 91.2 | 85.2 | 68.5 |
| | | % Secondary Amine | 1.9 | 2.4 | 3.7 | 5.2 |
| 0.68 | 14.5 | % Alcohol Conversion | 30.5 | 52.2 | 70.9 | 84.8 |
| | | % Primary Amine | 92.9 | 92.0 | 85.8 | 73.3 |
| | | % Secondary Amine | 1.9 | 2.0 | 3.4 | 5.1 |

EXAMPLE 4

Another run was performed using the reactor and reactor conditions described above and a reactor temperature of 230° C. Reactor effluent corresponding to a throughput of ca. 3372.5 g 2(2-methoxyethoxy)ethanol feed was collected. Distillation of this material afforded 841.6 g of starting alcohol (791.3 g distilled (bp 185°-190° C.), 50.3 g left in residue) which corresponded to 75.0% conversion. Also obtained was 1880.0 g 2-(2-methoxyethoxy)ethylamine (bp 167°-168.5° C.), which corresponded to a 74.9% yield based on unrecovered alcohol. Some dark residue (348.0 g) remained in the distillation pot. Gas chromatographic analysis indicated this material contained ca. 14.4% starting alcohol and 20.7% bis(2-(2-methoxyethoxy)ethyl)amine.

EXAMPLE 5

A sample of the Ni-Cu-Cr catalyst identical to that described in Example 1 was charged to a 1.337" ID tubular, upward flow, reactor. Ammonia and 2-(2-butoxyethoxy)ethanol were pumped through the catalyst bed at hourly feed rates of 1.69 lb (45.0 mol) and 1.61 lb (4.5 mol), respectively. The pressure was maintained at 2500 psig. Liquid samples corresponding to several reactor temperatures at both of two hydrogen feed rates were analyzed on a water and ammonia free basis. The results along with appropriate reactor conditions are given in Table III.

As will be observed from the foregoing examples, when the reactions were conducted within the reaction parameters of the present invention the acceptable conversions within the range of about 40 to about 75% were obtained. Moreover, the yield of the desired primary amine product was within the desired range of about 85 to about 95%, all based on the oxyalkylene glycol monoalkyl ether starting material.

Note with special reference to Example 3 that higher yields of primary amine were obtained at hydrogen to alcohol molar ratios of less than about 1.0 and ammonia to hydrogen ratios of greater than about 10. These reaction conditions correspond to a hydrogen partial pressure of much less than the 30% required in the Shirley et al. patent. In fact, the results of Example 3 suggest that if the hydrogen partial pressure were raised to 30% (i.e., mol NH$_3$ to mol hydrogen ratio of ca. 2.3) the yield of primary amine would be much lower in the case where alcohol reactant is one or more oxyalkylene glycol monoalkyl ethers.

Having this described our invention what is claimed is:

1. A process for the conversion of an oxyalkylene glycol monoalkyl ether to the corresponding primary amine, said monoalkyl ether having the formula:

$$[R(OCH_2CH_2)OH] \quad R(OCH_2CH_2)_xOH \quad (I)$$

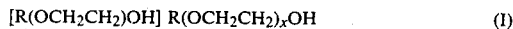

wherein R is an alkyl group containig 1 to 10 carbon atoms and x is an integer having a value of about 1 to about 5, said catalyst containing, as the active components, from about 50 to about 90 wt. % of nickel, about 10 to about 50 wt. % of copper and about 0.5 about 5 wt. % of an oxide selected from the class consisting of chromium oxide, iron oxide, titanium oxide, thorium oxide, zirconium oxide, manganese oxide, magnesium oxide and zinc oxide, said monoalkyl ether being brought into contact with said catalyst under liquid phase conversion conditions effective for the conversion of about 40% to about 80% of said monoalkyl ether including a temperature within the range of about 175° to about 250° C., and a pressure within the range of about 500 to about 5000 psig, said conversion being conducted in the presence of added hydrogen and added ammonia utilized in the proportions of about 0.3 to about 0.7 mole of hydrogen and about 4 to about 25 moles of ammonia per mole of said monoalkyl ether, the partial pressure of said hydrogen being less than 30%, whereby said monoalkyl ether is substantially selectively converted to the corresponding primary amine, and recovering said primary amine from the products of said reaction.

2. A method as in claim 1 wherein the catalyst contains from about 70 to about 77 wt. % of nickel, about 20 to about 25 wt. % of copper and about 2 to about 5 wt. % of chromium oxide.

3. A method as in claim 1 wherein the monoalkyl ether is an ethylene glycol monoalkyl ether.

4. A method as in claim 3 wherein the ether group contains 4 carbon atoms.

5. A method as in claim 3 wherein the ether group contains 1 carbon atom.

6. A method as in claim 1 wherein the monoalkyl ether is a diethylene glycol monoalkyl ether.

7. A method as in claim 6 wherein the ether group contains 1 carbon atom.

8. A method as in claim 6 wherein the ether group contains 4 carbon atoms.